(12) United States Patent
Yin et al.

(10) Patent No.: US 12,331,321 B1
(45) Date of Patent: Jun. 17, 2025

(54) ALPHA-HERPESVIRUS INSENSITIVE MONOCLONAL CELL STRAIN, AND PREPARATION METHOD THEREFOR AND USE THEREOF

(71) Applicant: Harbin Veterinary Research Institute, Chinese Academy of Agricultural Sciences (China Animal Health and Epidemiology Center Harbin Branch Center), Harbin (CN)

(72) Inventors: Xin Yin, Harbin (CN); Menghang Wang, Harbin (CN); Xing Liu, Harbin (CN)

(73) Assignee: Harbin Veterinary Research Institute, Chinese Academy of Agricultural Sciences (China Animal Health and Epidemiology Center Harbin Branch Center), Harbin (CN)

( * ) Notice: Subject to any disclaimer, the term of this patent is extended or adjusted under 35 U.S.C. 154(b) by 0 days.

(21) Appl. No.: 18/964,018

(22) Filed: Nov. 29, 2024

(30) Foreign Application Priority Data

Dec. 18, 2023 (CN) .......................... 202311733555.2

(51) Int. Cl.
*C12N 5/09* (2010.01)
*G01N 33/50* (2006.01)

(52) U.S. Cl.
CPC ....... *C12N 5/0693* (2013.01); *G01N 33/5032* (2013.01)

(58) Field of Classification Search
None
See application file for complete search history.

*Primary Examiner* — Nicole Kinsey White
(74) *Attorney, Agent, or Firm* — IPRO, PLLC; Na Xu (57) ABSTRACT

The present disclosure discloses an α-herpesvirus insensitive monoclonal cell strain, and a preparation method therefor and use thereof, belonging to the technical field of biomedicine. In order to perform targeted research of intercellular transmission of an α-herpesvirus and an action mechanism thereof, the present disclosure discloses the α-herpesvirus insensitive monoclonal cell strain. The cell strain is named as a human liver cancer continuous cell line Huh7-C10 and has a potential of being applied to developing a new generation of enhanced oncolytic herpesvirus and single-round infection attenuated live vaccine.

4 Claims, 13 Drawing Sheets

Specification includes a Sequence Listing.

α-herpesvirus receptor protein assay

SEQUENCE LISTING

```
Sequence total quantity: 3
SEQ ID NO: 1            moltype = DNA  length = 17
FEATURE                 Location/Qualifiers
source                  1..17
                        mol_type = other DNA
                        organism = synthetic construct
SEQUENCE: 1
aagaccccaa cgagaag                                                 17

SEQ ID NO: 2            moltype = DNA  length = 19
FEATURE                 Location/Qualifiers
source                  1..19
                        mol_type = other DNA
                        organism = synthetic construct
SEQUENCE: 2
tcgtccatgc cgagagtga                                               19

SEQ ID NO: 3            moltype = DNA  length = 27
FEATURE                 Location/Qualifiers
source                  1..27
                        mol_type = other DNA
                        organism = synthetic construct
```

```
SEQUENCE: 3
acatggtcct gctggagttc gtgaccg                                          27
```

ALPHA-HERPESVIRUS INSENSITIVE MONOCLONAL CELL STRAIN, AND PREPARATION METHOD THEREFOR AND USE THEREOF

REFERENCE TO SEQUENCE LISTING

The instant application contains a Sequence Listing in XML format as a file named "USAAA232125-seq.xml", created on Mar. 5, 2025, of 3894 bytes in size, and which is hereby incorporated by reference in its entirety.

TECHNICAL FIELD

The present disclosure belongs to the technical field of biomedicine, and in particular to an α-herpesvirus insensitive monoclonal cell strain, and a preparation method therefor and use thereof.

BACKGROUND

A-herpesviruses are human and animal comorbid viruses with neurotropism. Human α-herpesviruses include herpes simplex virus type 1 (HSV-1), herpes simplex virus type 2 (HSV-2) and varicella-zoster virus (VZV). In addition, the α-herpesviruses further include animal α-herpesviruses such as pseudorabies virus (PRV), equine herpesvirus type 1 (EHV-1), bovine herpesvirus type 1 (BHV-1), avian infectious laryngotracheitis virus (AILTV), Marek's disease virus (MDV), and the like. A great number of α-herpesviruses with neurotropism have been studied in depth so far, including HSV-1, HSV-2, VZV, PRV and BHV-1. But HSV-1 and PRV are most commonly studied as model viruses.

The α-herpesviruses have extensive tissue tropism and neuroinvasiveness. Once the viruses enter the peripheral or central nervous system, they undergo transsynaptic transmission between neurons, and cause damage to the nervous system or establish lifelong latent infections in the sensory neuron cell bodies. During the process of disease initiation by reactivation of latent infection, intercellular transmission is the main way for effective transmission of the α-herpesviruses. The intercellular transmission of the viruses avoids antiviral reaction of neutralizing antibodies and innate immune system, and meanwhile provides a more efficient and faster way for infection. However, there have been reported few host factors that regulate and control the intercellular transmission of the α-herpesvirus. The reasons lie in that: firstly, most of the current researches mainly aim at virus important glycoproteins gD, gH, gL, gB, gE and gI, and only screen target proteins interacting with the above few glycoproteins, thereby omitting important host factors interacting with other structural proteins or non-structural proteins; and secondly, host factors for regulating and controlling the intercellular transmission of the α-herpesviruses are directly searched by utilizing genomics or proteomics, but a plurality of candidate genes cause great screening difficulty and the stage of the intercellular transmission of the α-herpesviruses cannot be targeted. Therefore, the scientific problem of how to regulate and control the intercellular transmission of the α-herpesviruses and an action mechanism thereof by the host factors remains to be solved urgently.

In conclusion, the intercellular transmission mechanism of the α-herpesviruses, especially the molecular mechanism of how to seize host cell machines to complete the life cycle thereof, is not clear, thereby hindering the development and application of novel diagnostic and therapeutic preparations. Therefore, fundamental research on the intercellular transmission of the α-herpesviruses is urgently needed.

SUMMARY

The objective of present disclosure is to provide a cell strain and method that can perform targeted research of intercellular transmission of an α-herpesvirus and an action mechanism thereof.

The present disclosure provides an α-herpesvirus insensitive monoclonal cell strain, where the cell strain is named as a human liver cancer continuous cell line Huh7-C10 and deposited in the China General Microbiological Culture Collection Center with a deposit number of CGMCC NO. 45727 on Oct. 7, 2023.

Further defined, the human liver cancer continuous cell line Huh7-C10 is insensitive when infected with an α-herpesvirus.

Further defined, the insensitivity refers to an incapability of intercellular diffusion in the human liver cancer continuous cell line Huh7-C10.

The present disclosure provides the above-mentioned α-herpesvirus monoclonal cell strain, where the α-herpesvirus is herpes simplex virus type 1, bovine herpesvirus type 1 and porcine pseudorabies virus.

The present disclosure provides a method for preparing the above-mentioned α-herpesvirus monoclonal cell strain, including the following specific steps: culturing a commercial cell Huh-7, sorting single cell clones into a 96-well plate using flow cytometry, infecting the single cell clones with an α-herpesvirus labeled with a green fluorescent protein (HSV-1-GFP) at MOI of 0.1, and screening a single cell strain with a poor infection ability of the α-herpesvirus through the fluorescence intensity.

The present disclosure provides use of the human liver cancer continuous cell line Huh7-C10 in establishing a model of an intercellular transmission mechanism of the above-mentioned α-herpesvirus.

Further defined, the use is for non-diagnostic and therapeutic purposes.

The present disclosure provides a method for establishing a model of an intercellular transmission mechanism of an α-herpesvirus, where the method includes the following specific steps: on the basis of differences between the human liver cancer continuous cell line Huh7-C10 and a commercial cell Huh-7, information of host factors for regulating and controlling intercellular transmission of an α-herpesvirus is obtained by using genomics or proteomics.

Beneficial effects: starting from the point of view of host cells, the present disclosure cultures and screens a commercial cell Huh-7, prepares single cell clones, infects the single cell clones with an α-herpesvirus labeled with a green fluorescent protein (HSV-1-GFP), and screens an α-herpesvirus insensitive monoclonal cell strain Huh7-C10 through the fluorescence intensity. A series of tests are performed to analyze which specific stage of α-herpesvirus infection is not supported by the insensitive Huh7-C10 cell. It is found that the Huh7-C10 cell only specifically influence the intercellular transmission of the α-herpesvirus, indicating that the insensitive cell strain Huh7-C10 can be used as a unique cell model for researching intercellular diffusion of the α-herpesvirus.

Transcriptomics analysis shows that there are only 210 differential genes between the human liver cancer continuous cell line Huh7-C10 and the commercial cell Huh-7, including 198 down-regulated genes and 12 up-regulated genes. A bioinformatics tool is used for performing enrichment analysis to anchor key target genes for regulating and controlling the intercellular transmission of the α-herpesvirus, and exploring a molecular mechanism of the α-herpesvirus for rapid transmission realized by seizing host cell machines, such that the infection transmission mechanism of the α-herpesvirus can be updated and the cell line has the potential of being applied to developing a new generation of enhanced oncolytic herpesvirus and single-round infection attenuated live vaccine.

[Biological deposit information]: a human liver cancer continuous cell line Huh7-C10 is deposited in the China General Microbiological Culture Collection Center in No. 3 Yard 1, West Beichen Road, Chaoyang District, Beijing, with a deposit number of CGMCC NO. 45727 on Oct. 7, 2023.

BRIEF DESCRIPTION OF FIGURES

FIG. 1A-1D shows results of infection by PRV, HSV-1 and BHV-1 influenced by a human liver cancer continuous cell line Huh7-C10.

FIG. 2A-2C shows results of cell characteristics of the human liver cancer continuous cell line Huh7-C10.

FIG. 3A-3F shows the results that a single-round life cycle of an α-herpesvirus in the human liver cancer continuous cell line Huh7-C10 is not influenced.

FIG. 4A-4C shows the results of limiting of intercellular diffusion of the α-herpesvirus in the human liver cancer continuous cell line Huh7-C10: FIG. 5A-5C shows results of host differential candidate genes that regulate and control intercellular transmission of the α-herpesvirus.

DETAILED DESCRIPTION

The commercial cell Huh-7 (human liver cancer cell) is the source cell of the human liver cancer continuous cell line Huh7-C10 and purchased from Wuhan Yipu Biotechnology Co., Ltd with the article number of CL-0120.

rPRVTJ-Nluc is recorded in Wang Y, Wu H, Wang B, Qi H, Jin Z, Qiu H J, Sun Y. A NanoLuc Luciferase Reporter Pseudorabies Virus for Live Imaging and Quantification of Viral Infection. Front Vet Sci. 2020 Sep. 22; 7:566446. doi: 10.3389/fvets.2020.566446. PMID: 33195544; PMCID: PMC7537659.

HSV-1-GFP is recorded in the already published article: Wang Y, Wu H, Wang B, Qi H, Jin Z, Qiu H J, Sun Y. A NanoLuc Luciferase Reporter Pseudorabies Virus for Live Imaging and Quantification of Viral Infection. Front Vet Sci. 2020 Sep. 22; 7:566446. doi: 10.3389/fvets.2020.566446. PMID: 33195544; PMCID: PMC7537659.

PRV-GFP is a PRV labeled by a green fluorescent protein which is labeled in a PRV viral genome UL24.

Example 1 Method for Obtaining Human Liver Cancer Continuous Cell Line Huh7-C10

1. Experimental method: a commercial cell Huh-7 was purchased and grew in a cell incubator with 5% $CO_2$ at 37° C., subsequently, the cells were dispersed into single cells by using a 0.25% trypsin solution, the cell suspension was taken and filtered by a filter screen, the filtered cell suspension was added into a special tube for flow cytometry, mixed evenly and loaded into a flow cytometry sorting system SONY-MA900, and the commercial cell Huh-7 single cell strain was sorted into a 96-well plate for culture. After the commercial cell Huh-7 single cell strain grew to a monolayer, the commercial cell Huh-7 single cell strain infected by a green fluorescent protein-labeled α-herpesvirus (HSV-1-GFP) with a MOI of 0.1, and the single cell strain was screened through the fluorescence intensity.

2. Experimental results: after the Huh-7 was subjected to the flow cytometric sorting, a vast majority of the single cell strains were susceptible to an α-herpesvirus, where a susceptible cell strain C7 was a selected representative single cell strain. Few single cell strains appeared to be insensitive to the α-herpesvirus, where a human liver cancer continuous cell line Huh7-C10 was a selected representative single cell strain.

Example 2 Human Liver Cancer Continuous Cell Line Huh7-C10 does not Support Infection by α-Herpesvirus 1. Experimental method: the commercial cell Huh-7, the susceptible cell strain C7 and the human liver cancer continuous cell line Huh7-C10 were cultured into a 96-well plate. The three different cells were infected by using a herpes simplex reporter virus labeled with a green fluorescent protein (HSV-1-GFP) with the infection dose MOI of 0.1 or a pseudorabies reporter virus labeled with a green fluorescent protein (PRV-GFP) with the infection dose MOI of 0.01. The fluorescence intensities of the viruses after infection at time points of 0 h, 12 h, 24 h, 36 h and 48 h were observed and photographed under an inverted fluorescence microscope.

2. The commercial cell Huh-7, the susceptible cell strain C7 line and the insensitive monoclonal cell strain Huh7-C10 were also cultured in a 96-well plate. The three different cells were infected with a wild-type bovine herpesvirus type 1 (BHV-1) with the infection dose MOI of 0.1. After 48 h of the infection, the cytopathic effects (CPE) caused by the viruses were detected by the inverted microscope.

3. The commercial cell Huh-7, the susceptible cell strain C7 and the human liver cancer continuous cell line Huh7-C10, and viral solutions of porcine pseudorabies virus (PRV), herpes simplex virus (HSV-1), vesicular stomatitis virus (VSV) and vaccinia virus (VACV) were prepared. After the three cells were inoculated with the viral solutions with the infectious dose MOI of $10^{-4}$ for 2 h, a cell maintenance solution containing 1% of agarose at a low melting point (Beyotime, ST105) was added, and the mixture was cooled in a refrigerator at 4° C. for 30 min to solidify into a coating layer. After 2-3 days of culture, when plaques were evident observed under a microscope, a 1% crystal violet solution was added to each well to cover the cell surface, and the cells were allowed to stand for 30 min at room temperature for staining. After the cells were slowly rinsed clean with tap water, the cells were air-dried to observe the results. The sizes of plaques formed by three viruses infecting different cells were compared by using a virus plaque assay.

Figure 1A:
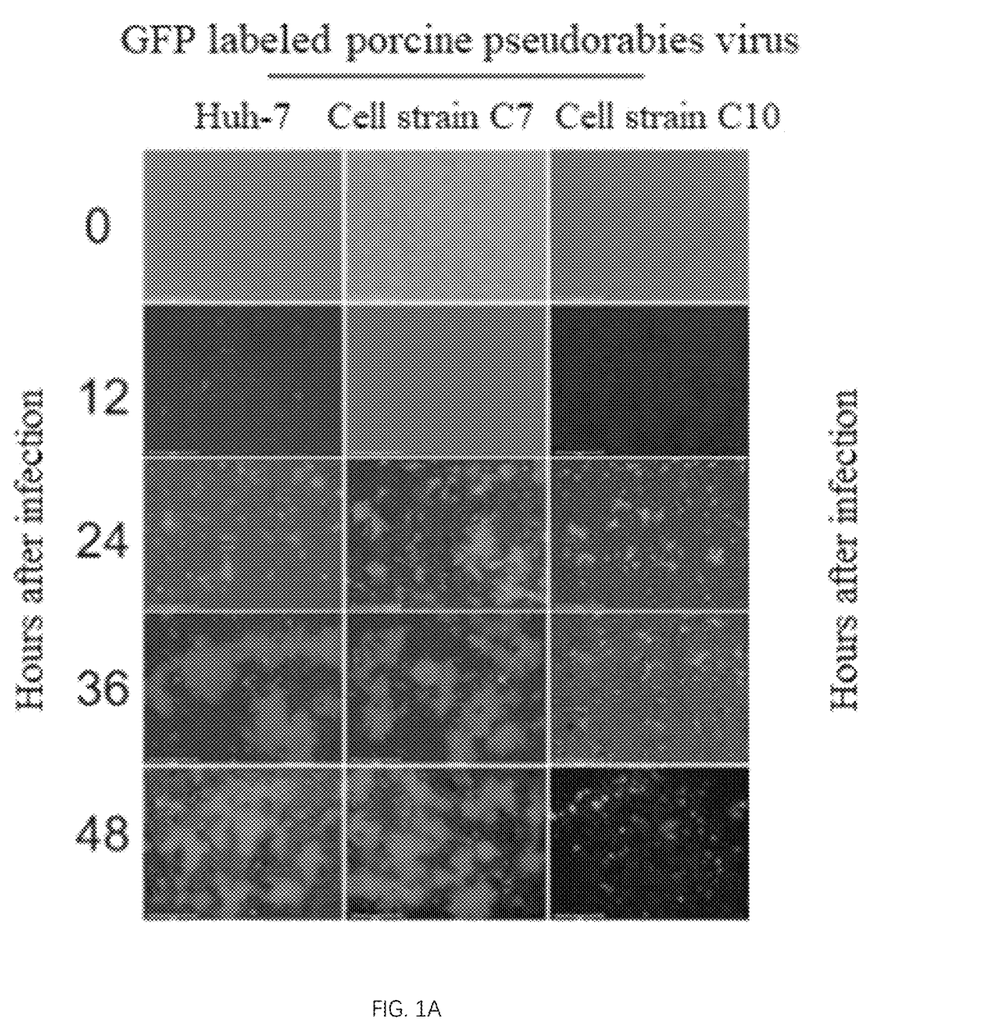
FIG. 1A: fluorescence images of a commercial cell Huh-7 (Huh-7), the human liver cancer continuous cell line Huh7-C10 (cell strain C10) and a susceptible monoclonal cell C7 (cell strain C7) infected by an α-herpesvirus PRV-GFP.
Figure 1B:
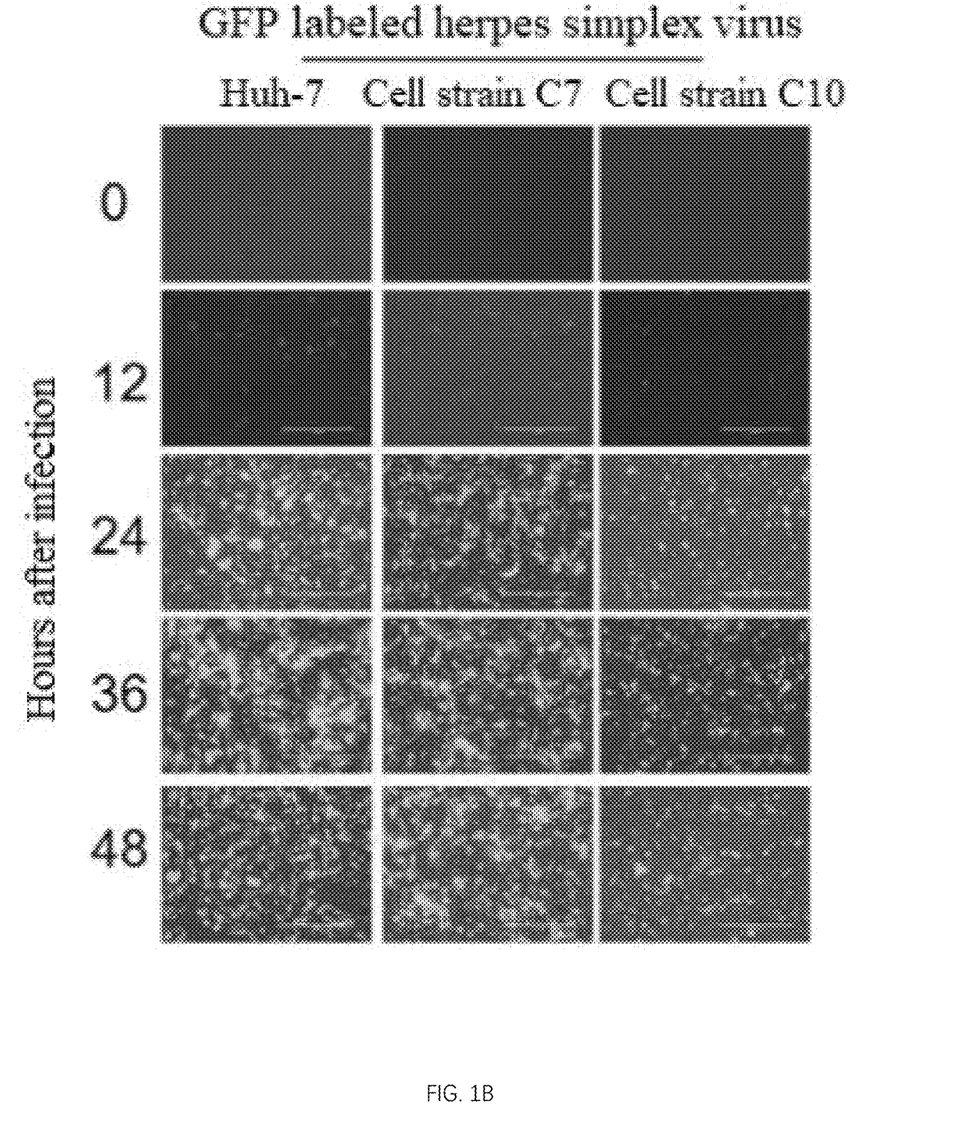
FIG. 1B: fluorescence images of the commercial cell Huh-7 (Huh-7), the human liver cancer continuous cell line Huh7-C10 (cell strain C10) and the susceptible monoclonal cell C7 (cell strain C7) infected by HSV-1-GFP.
Figure 1C:
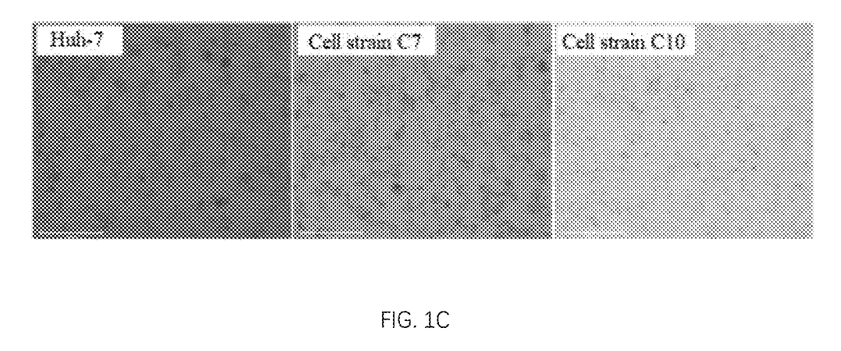
FIG. 1C: cytopathic results of the commercial cell Huh-7 (Huh-7), the human liver cancer continuous cell line Huh7-C10 (cell strain C10) and the susceptible monoclonal cell C7 (cell strain C7) infected by BHV-1.
Figure 1D:
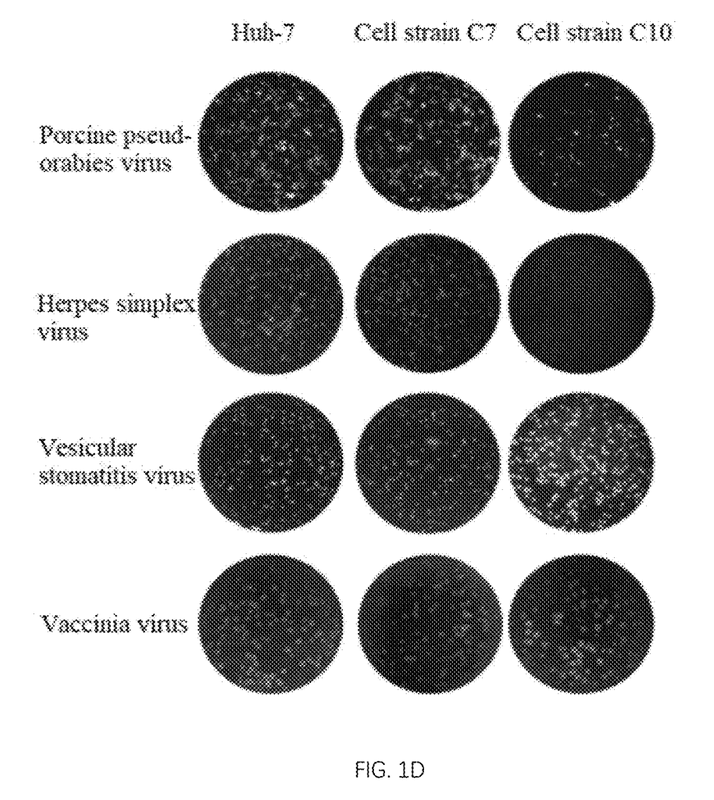
FIG. 1D: susceptibility results of the commercial cell Huh-7 (Huh-7), the human liver cancer continuous cell line Huh7-C10 (cell strain C10) and the susceptible monoclonal cell C7 (cell strain C7) to PRV, HSV-1, VSV and VACV analyzed by a virus plaque assay.

4. Experimental results: the commercial cell Huh-7, the susceptible cell strain C7 and the insensitive monoclonal cell strain Huh7-C10 were infected by PRV-GFP. After the virus inoculation for 24 h, the infection proportion of the α-herpesvirus in the human liver cancer continuous cell line Huh7-C10 was low and the viruses were distributed in a single cell manner. In the commercial cell Huh-7 and the susceptible cell strain C7, the virus infection formed large syncytia (FIG. 1A). After the three different cells were infected by HSV-1-GFP and BHV-1, it was found that the infection of the α-herpesvirus by HSV-1-GFP and BHV-1 was limited as well in the human liver cancer continuous cell line Huh7-C10 (FIGS. 1B and 1C). Subsequently, it was further verified by the virus plaque assay that PRV and HSV-1 had relatively small and less plaques in the human liver cancer continuous cell line Huh7-C10. More noteworthy, the infection ability of the human liver cancer continuous cell line Huh7-C10 was stronger than that of the commercial cell Huh-7 and susceptible cell strain C7 during the infection process with the RNA control virus VSV and the DNA control virus VACV. Therefore, the human liver cancer continuous cell line Huh7-C10 only specifically limited the infection with the α-herpesvirus (FIG. 1D).

Example 3 Characteristic Study of Human Liver Cancer Continuous Cell Line Huh7-C10

1. Experimental method: the commercial cell Huh-7, the susceptible cell strain C7 and the human liver cancer continuous cell line Huh7-C10 were inoculated into a 6-well plate. The sizes, shapes, growth states of the cells were observed through the inverted microscope. The commercial cell Huh-7, the susceptible cell strain C7 and the human liver cancer continuous cell line Huh7-C10 were inoculated into a 96-well plate and cultured until the time points of 6 h, 12 h, 24 h, 36 h, 48 h and 72 h, 100 µl of a CCK-8 detection solution was added into each well, the cells were incubated at 37° C. for 2 h, and the absorbance of each well at the wavelength of 450 nm was detected by using a microplate reader to detect the cell proliferation. Total RNAs of the commercial cell Huh-7, a commercial liver cancer control cell (HepG2, ATCC, HB-8065), the susceptible cell strain C7 and the human liver cancer continuous cell line Huh7-C10 were respectively extracted and sent to the BGI Tech, and subjected to RNA-seq sequencing on a high-throughput Illumina platform. Sequencing data was subjected to a principal component analysis (PCA) in a multivariate data analysis by using a Dr. Tom analysis software in the BGI Tech, which can represent the overall expression pattern of all genes and thus describe sample differences.

Figure 2A:
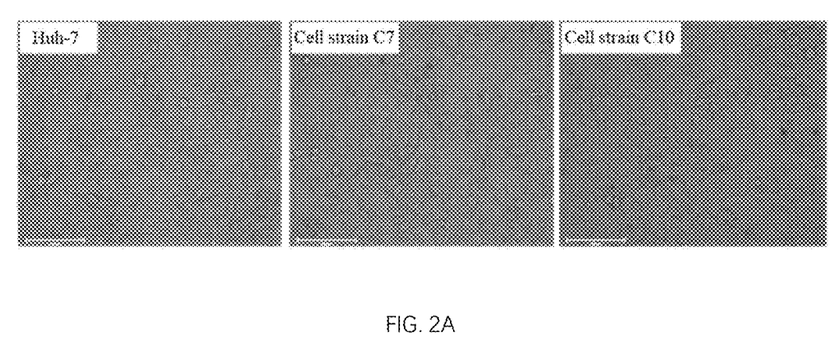
FIG. 2A: morphological characteristics of the commercial cell Huh-7 (Huh-7), the human liver cancer continuous cell line Huh7-C10 (cell strain C10) and the susceptible monoclonal cell C7 (cell strain C7) observed by a microscope.
Figure 2B:
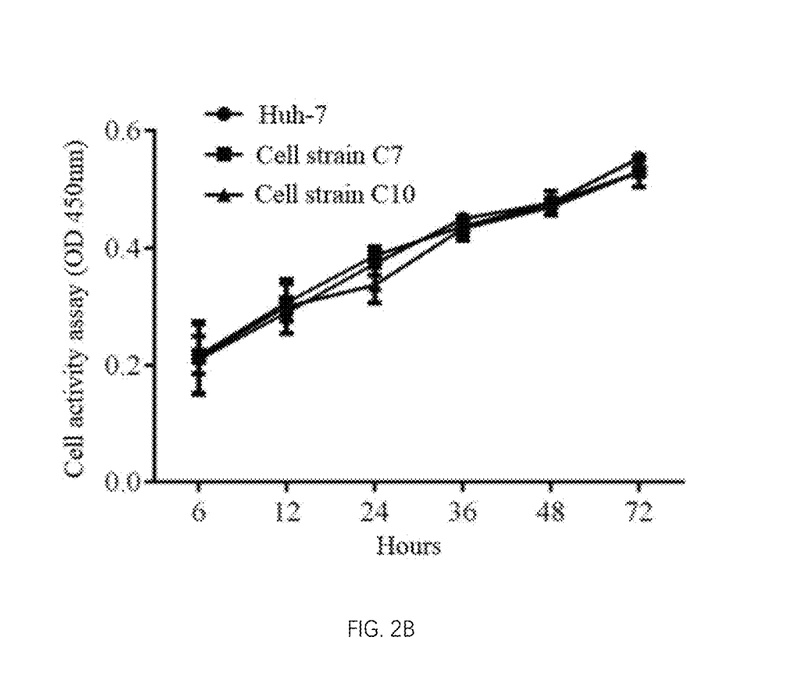
FIG. 2B: cell activity and proliferation results of the commercial cell Huh-7 (Huh-7), the human liver cancer continuous cell line Huh7-C10 (cell strain C10) and the susceptible monoclonal cell C7 (cell strain C7) detected by CCK-8.
Figure 2C:
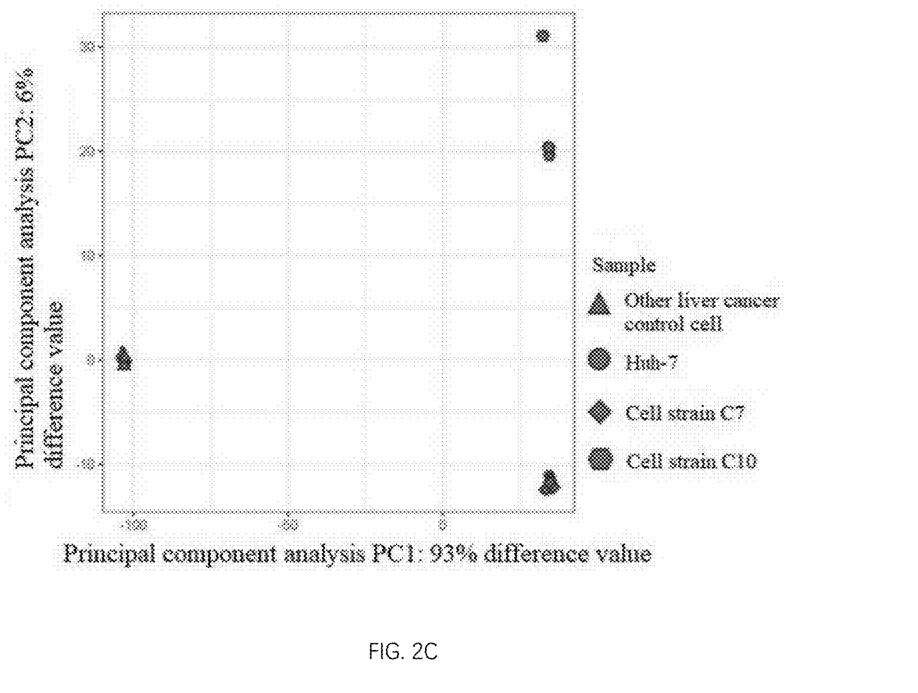
FIG. 2C: similarity results of the commercial cell Huh-7 (Huh-7), the susceptible monoclonal cell C7 and the human liver cancer continuous cell line Huh7-C10 analyzed by PCA.

2. Experimental results: the sizes, shapes, growth states of the commercial cell Huh-7 and the subclone cell strains (the susceptible cell strain C7 and the human liver cancer continuous cell line Huh7-C10) were observed by the inverted microscope. It was found that there was no significant difference between the three cells (FIG. 2A). The cell activity and proliferation of the commercial cell Huh-7, the susceptible cell strain C7 and the human liver cancer continuous cell line Huh7-C10 were detected by using a CCK-8 analysis. It was found that there was no significant difference between the three cells (FIG. 2B). In order to further determine that the human liver cancer continuous cell line Huh7-C10 was a subclone strain of the commercial cell Huh-7, the differences of the commercial cell Huh-7, the susceptible cell strain C7, the human liver cancer continuous cell line Huh7-C10 and other liver cancer control cell (HepG2) on the gene transcription level were analyzed through RNA-seq. The PCA showed that the human liver cancer continuous cell line Huh7-C10 had extremely high similarity with the commercial cell Huh-7 and low similarity with the control liver cancer cell HepG2 (FIG. 2C). The study results proved that the human liver cancer continuous cell line Huh7-C10 was derived from the commercial Huh-7 cell line.

Example 4 Analysis of Infection Characteristics of α-Herpesvirus in Human Liver Cancer Continuous Cell Line Huh7-C10

1. Experimental method: the commercial cell Huh-7, the susceptible cell strain C7 and the human liver cancer continuous cell line Huh7-C10 were cultured in a 6-well plate overnight. When the cells grew to a monolayer, 200 µl of an IP cell lysate (Beyotime, P0013) was used per well and cell protein samples were collected. An α-herpesvirus major receptor protein Nectin-1 (Nectin-1 antibody brand: Santa Cruz Biotechnology, article number of sc-21722) endogenously expressed in three different cells were detected by WB. In the same way, important signal transduction linker proteins PAK1, RHOA, RAC1 and CDC42 (PAK1, RHOA, RAC1 and CDC42 antibody brand: Cell Signaling Technology, article number of 2602S, 2117S, 2465S and 2462S) of three different cellular macropinocytosis signal pathways were detected by WB. The expression amounts of key proteins related to the absorption and invasion processes of the α-herpesvirus in the three different cells were analyzed.

2. The commercial cell Huh-7, the susceptible cell strain C7 and the human liver cancer continuous cell line Huh7-C10 were cultured in a 24-well plate overnight. When the cells grew to a monolayer, the cells were divided into two groups, namely a DNA inhibitor drug treatment group and a control group. The DNA inhibitor drug was cytarabine (Sigma-Aldrich, PHR1787) with the final concentration of 300 ng/ml. Subsequently, after the three different cells were infected with HSV-1-GFP with MOI of 0.1 for 2 h, a cell culture solution containing 300 ng/ml of cytarabine was added to the DNA inhibitor drug treatment group, and the cell culture solution was only added in the control group. After the infection for 24 h, the infection was observed and photographed under the inverted fluorescence microscope.

3. The commercial cell Huh-7, the susceptible cell strain C7 and the human liver cancer continuous cell line Huh7-C10 were infected with rPRVTJ-Nluc with the high dose MOI of 5. The luciferase activities at two time points of 6 h and 12 h after the infection were detected by using a multifunctional microplate reader (PerkinElmer company) under the high-dose infection so as to analyze whether a genome replication stage of the α-herpesvirus infection was influenced by the human liver cancer continuous cell line Huh7-C10 or not.

4. After HSV-1-GFP with MOI of 5 infected the commercial cell Huh-7, the susceptible cell strain C7 and the human liver cancer continuous cell line Huh7-C10 for 8 h, viral solutions released into supernatants were harvested. By designing specific primers (GFP-F: AAGACCC-CAACGAGAAG, SEQ ID NO. 1; GFP-R: TCGTC-CATGCCGAGAGTGA, SEQ ID NO. 2; GFP-probe: ACATGGTCCTGCTGGAGTTCGTGACCG, SEQ ID NO. 3) of a GFP label in recombinant viruses, the gene copy number of the recombinant viruses in the supernatants were detected by using a fluorescent quantitative PCR method. Meanwhile, the collected virus supernatants were serially diluted by 10 times and respectively inoculated into the commercial cell Huh-7. Green fluorescence of the cells infected with the viruses was observed after 2 days. The number of wells with the highest dilution of the viruses capable of infecting the cells was taken as an end point. Finally, 50% tissue culture infectious dose ($TCID_{50}$) was calculated by a Reed&Muench statistical method. The content of infectious virions in the supernatant was detected. Whether the assembly and the release of the infectious virions in the different cells have difference or not was determined.

Figure 3A:
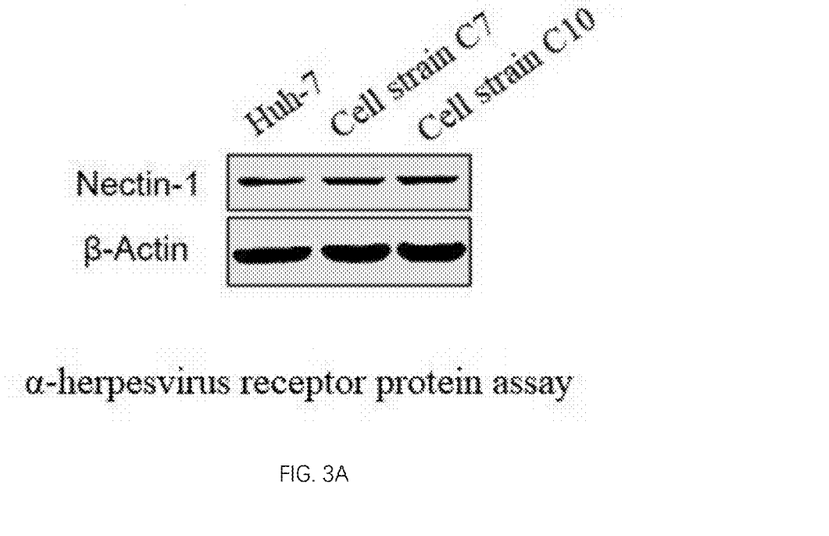
FIG. 3A: results of α-herpesvirus cell receptor Nectin-1 detected by WB.

5. Experimental results: to analyze at what stage the α-herpesvirus was affected in the infection of the human liver cancer continuous cell line Huh7-C10, the following studies were respectively performed:

(1) Expression of cell receptor: the expression of the α-herpesvirus major receptor protein Nectin-1 was detected by western blotting and no difference in the expression among the three cells was found (FIG. 3A).

Figure 3B:
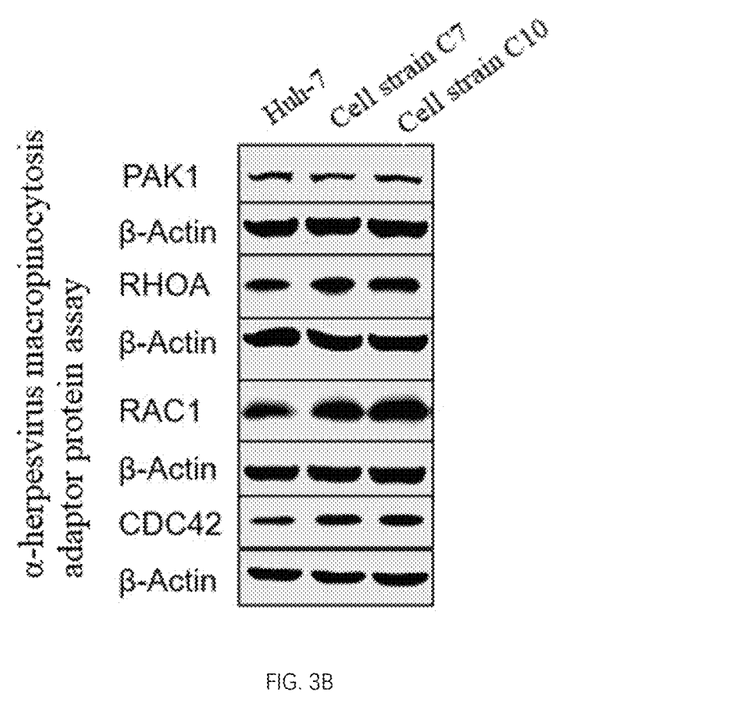
FIG. 3B: results of protein contents of 4 important signal transduction proteins for endocytosis.

(2) Detection of macropinocytosis pathway key proteins: the α-herpesvirus entered cells through the macropinocytosis. By detecting the protein contents of macropinocytosis key proteins PAK1, RHOA, RAC1 and CDC42, it was found that the expressions of the macropinocytosis key adaptor proteins were not different in the commercial cell Huh-7, the susceptible cell strain C7 and the human liver cancer continuous cell line Huh7-C10 (FIG. 3B), indicating that the α-herpesvirus was not influenced in the early infection stage of the human liver cancer continuous cell line Huh7-C10.

Figure 3C:
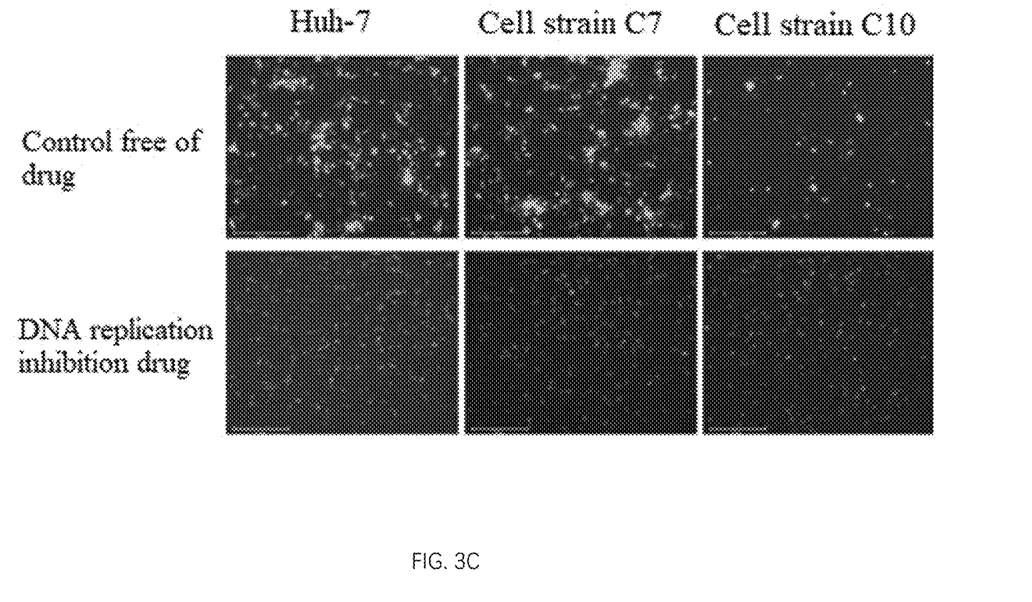
FIG. 3C: infection results of HSV-1-GFP in three different cells under the action of a DNA replication inhibitor drug or not by an inverted fluorescence microscope.

(3) Determination of virus adsorption and invasion: cytarabine was used as the DNA inhibitor drug to treat the cells infected by the viruses and whether the differences existed during adsorption and invasion processes before DNA replication of the viruses was detected. The results showed that after the DNA inhibitor drug treatment, the infection abilities of the α-herpesvirus in the human liver cancer continuous cell line Huh7-C10 and the commercial cell Huh-7 were not obviously different (FIG. 3C), indicating that the adsorption and invasion processes of the α-herpesvirus in the human liver cancer continuous cell line Huh7-C10 before the DNA replication were not limited.

Figure 3D:
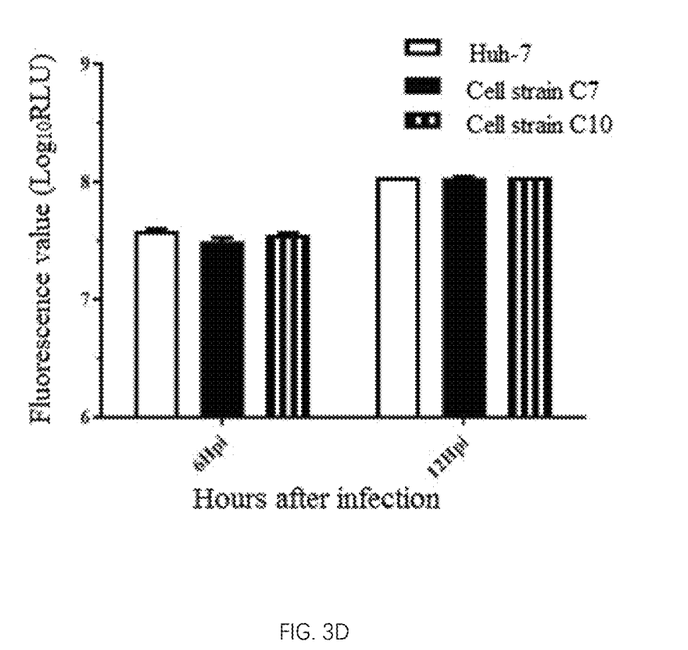
FIG. 3D: Luc fluorescence signal results of rPRVTJ-Nluc infected commercial cell Huh-7 and subclone strains with MOI of 5 detected by a microplate reader.

(4) Determination of replication capacity of viruses: the three cells were infected with rPRVTJ-Nluc with MOI of 5 and luciferase signals at 6 h and 12 h after the infection were detected by the microplate reader. The results showed that replication of a viral genome of the α-herpesvirus was not affected in the commercial cell Huh-7, the susceptible cell strain C7 and the human liver cancer continuous cell line Huh7-C10 (FIG. 3D).

Figure 3E:
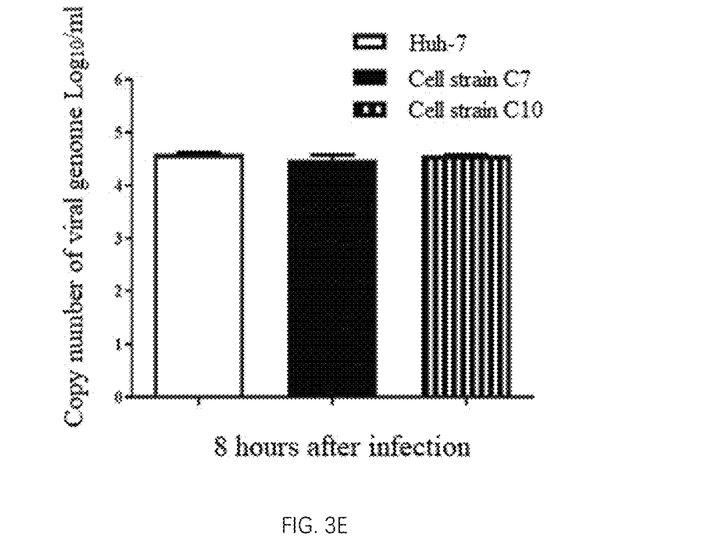
FIG. 3E shows the results of the gene copy number of the viruses in a cell supernatant at 8 h after HSV-1-GFP infection with MOI of 5.
Figure 3F:
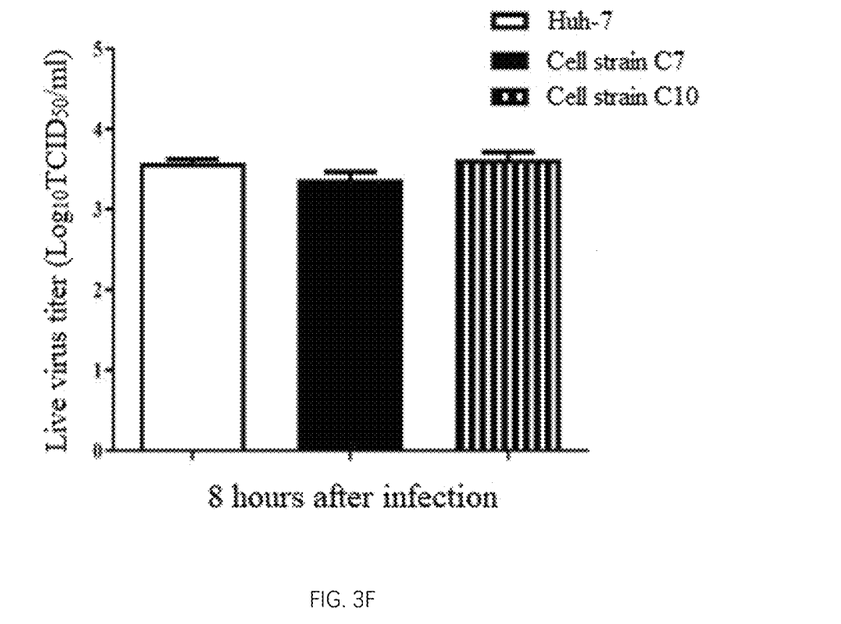
FIG. 3F shows the results of $TCID_{50}$ of the viruses in the cell supernatant at 8 h after HSV-1-GFP infection with MOI of 5.

(5) Determination of virus release capacity: by harvesting and detecting the content of the virions released into the supernatant after the infection of HSV-1-GFP with MOI of 5, it was found that the number of the viral genomes released from the commercial cell Huh-7, the C7 susceptible cells and the human liver cancer continuous cell line Huh7-C10 was equivalent, and the infection ability of the virions was similar (FIGS. 3E and 3F), indicating that the release capacity of the α-herpesvirus in the human liver cancer continuous cell line Huh7-C10 was not limited.

Example 5 Limiting of Intercellular Diffusion of α-Herpesvirus in Human Liver Cancer Continuous Cell Line Huh7-C10

1. Experimental method: the commercial cell Huh-7, the susceptible cell strain C7 and the human liver cancer continuous cell line Huh7-C10 were cultured into a 96-well plate overnight until the cells grew to a monolayer. The three different cells were infected by using rPRVTJ-Nluc with low dose MOI of 0.01 and the cell samples after 6 h, 12 h, 24 h, 36 h and 48 h of the infection were harvested. NanoLuc luciferase was detected by using a luciferase detection kit (Promega, N1110) and luciferase activity data at different time points was read by using the multifunctional microplate reader (PerkinElmer company).

2. $10^5$ commercial cells Huh-7 and human liver cancer continuous cell line Huh7-C10 were respectively cultured in a laser confocal cuvette (NEST, 801001), infected for 2 h, 6 h, 10 h, 16 h and 24 h by HSV-1-GFP with MOI of 0.1, and fixed with a 4% paraformaldehyde fixing solution (Beyotime, P0099) for 15 min. Then cell nuclei were stained by a DAPI staining agent (Beyotime, Huh7-C1005) and finally photographed by a high-resolution living cell confocal microscope (ZEISS, LSM800).

3. The commercial cell Huh-7, the susceptible cell strain C7 and the human liver cancer continuous cell line Huh7-C10 were prepared and cultured in a 6-well plate until the cells grew to a monolayer. After the three cells were respectively inoculated with the HSV-1-GFP viral solution with the infection dose MOI of $10^{-4}$ for 2 h, the cell maintenance solution containing 1% of agarose at a low melting point (Beyotime, ST105) was added, and the mixture was cooled in a refrigerator at 4° C. for 30 min to solidify into the coating layer. After the cells were placed in the cell incubator for 6 days, the cells were photographed by the inverted fluorescence microscope.

Figure 4A:
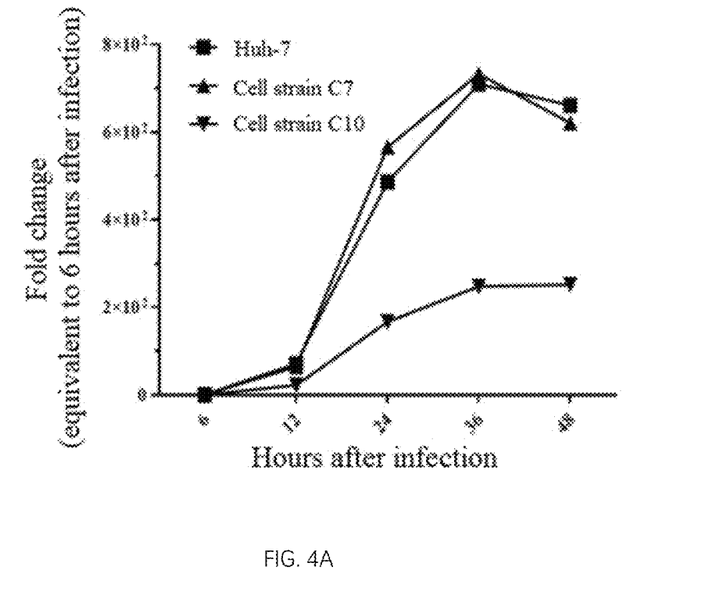
FIG. 4A: Luc fluorescence signal results of rPRVTJ-Nluc infected commercial cell Huh-7 and the subclone cell strains with MOI of 0.01 detected by the microplate reader.
Figure 4B:
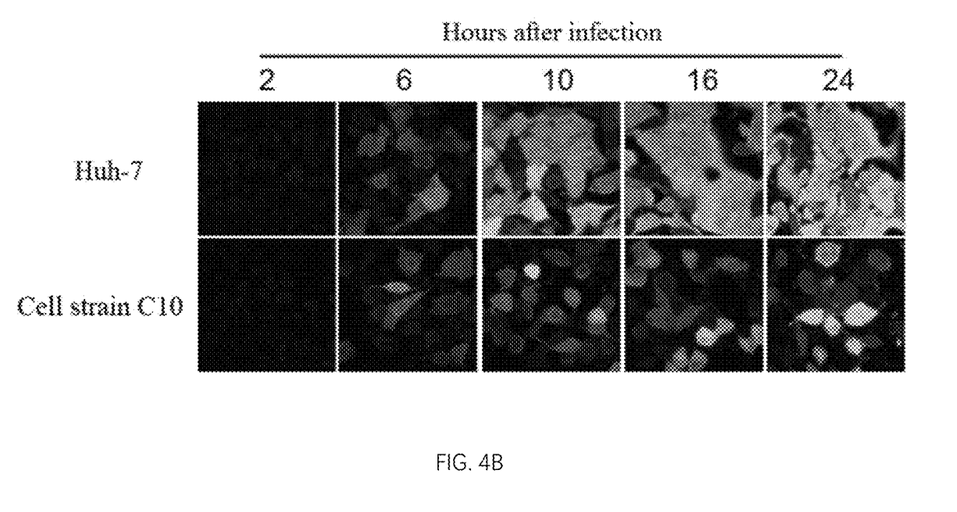
FIG. 4B: results of syncytia formed by the commercial cells Huh-7 and the subclone cell strains infected with HSV-1-GFP observed by a laser confocal microscope.
Figure 4C:
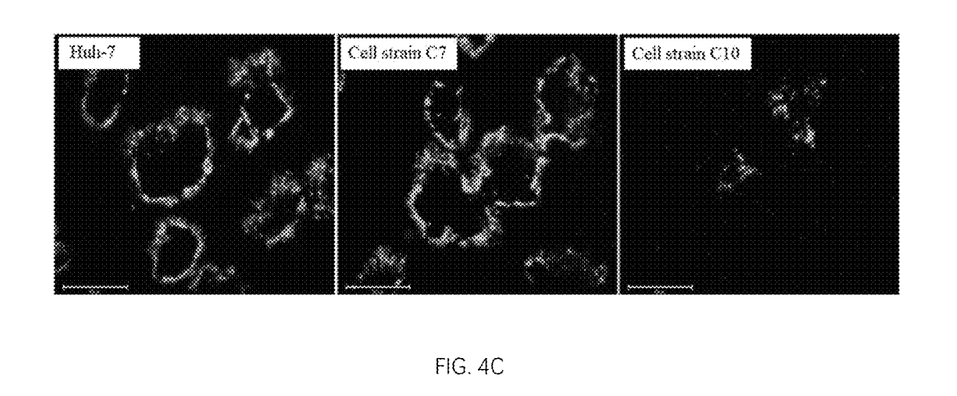
FIG. 4C: plaque fluorescence results of the commercial cell Huh-7 and the subclone cell strains infected with HSV-1-GFP.

4. Experimental results: the three different cells were infected with rPRVTJ-Nluc with MOI of 0.01 and the cells were collected at different time points. By detecting the luciferase activity, it was found that the α-herpesvirus had weaker amplification ability in the human liver cancer continuous cell line Huh7-C10 than other cells (FIG. 4A), indicating that the human liver cancer continuous cell line Huh7-C10 did not support multiple rounds of infection by the α-herpesvirus. It was found by the laser confocal microscopy that the α-herpesvirus infection could not form syncytia in the human liver cancer continuous cell line Huh7-C10 (FIG. 4B). Meanwhile, compared with the commercial cell Huh-7 and the susceptible cell strain C7, fluorescent virus plaques generated by HSV-1-GFP infected human liver cancer continuous cell line Huh7-C10 were remarkably reduced, proving that the intercellular diffusion of the α-herpesvirus in the human liver cancer continuous cell line Huh7-C10 was limited (FIG. 4C).

Example 6 Discovery of Host Factors for Regulating and Controlling Intercellular Transmission of α-Herpesvirus 1. Experimental method: the total RNAs of the commercial cell Huh-7, the commercial liver cancer control cell (HepG2, ATCC, HB-8065), the susceptible cell strain C7 and the human liver cancer continuous cell line Huh7-C10 were extracted respectively. The total RNA samples were sent to the BGI Tech and subjected to RNA-seq sequencing on the high-throughput Illumina platform. The sequencing data was analyzed by using the Dr. Tom analysis software in the BGI Tech. The differences of whole gene expression values among the samples were compared and analyzed by using the difference threshold values of log 2FoldChange>2 or log 2FoldChange<-2 and padj<0.05, and the volcano plot was drawn. Subsequently, the data of the differential genes was analyzed by using a GO enrichment tool in the Dr. Tom analysis software, and the cell component results described by the differential genes and the biological processes described by the differential genes were analyzed.

Figure 5A:
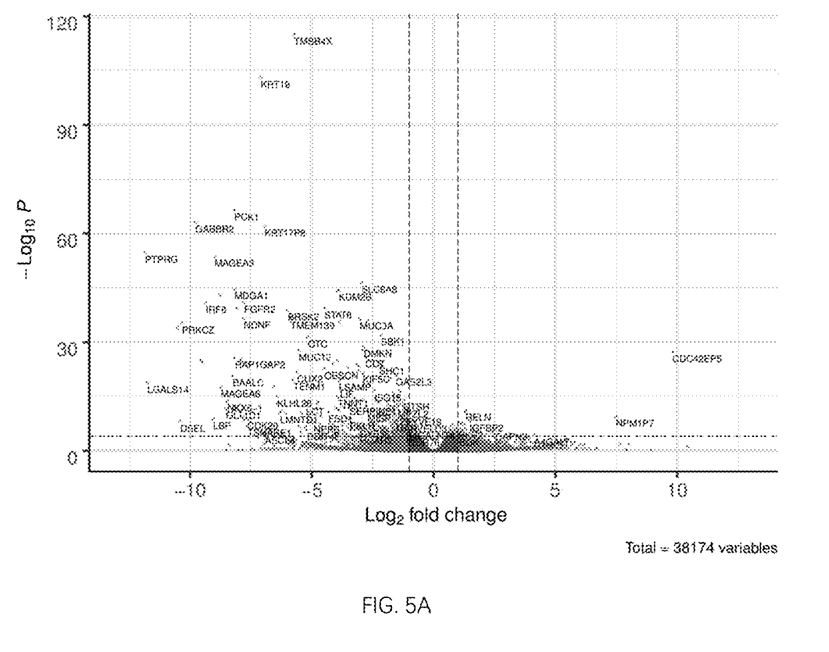
FIG. 5A: a volcano plot of differential genes between the human liver cancer continuous cell line Huh7-C10 and the commercial cell Huh-7.
Figure 5B:
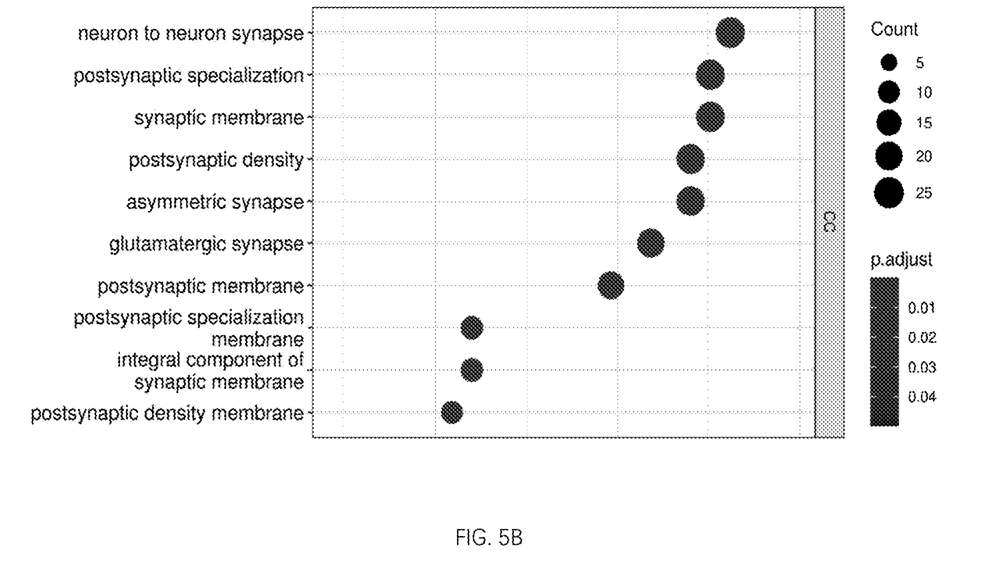
FIG. 5B: results of cell components described by the differential genes analyzed by a GO enrichment.
Figure 5C:
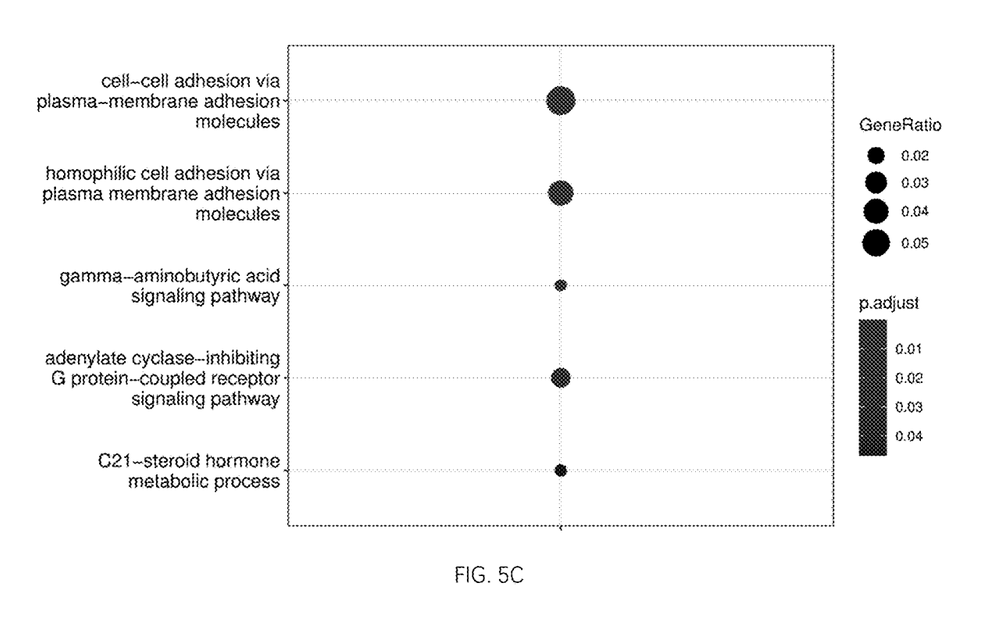
FIG. 5C: results of biological processes described by the differential genes analyzed by the GO enrichment.

2. Experimental results: it was found by sequencing analysis of transcriptomics that the expressions of only 210 genes of the human liver cancer continuous cell line Huh7-C10 and the commercial cell Huh-7 were obviously different, including 198 down-regulated genes and 12 up-regulated genes. DEseq2 was used for analyzing differential expression and the volcano plot was drawn. The comparative groups were set as human liver cancer continuous cell line Huh7-C10 vs commercial cell Huh-7. The results showed (FIG. 5A) that among the down-regulated genes, the fold change was large and the genes with very significant differences were: TMSB4X, KRT19, KRT17P8 and BRSK2, which were functionally related to the formation of cytoskeleton and regulation and control of recombination of actin cytoskeleton. In addition, GABBR2, NDNF and MDGA1 were also included. Their functions were associated with the formation and maintenance of cellular synapses and the promotion of the formation of neuronal processes. Subsequently, the data was further analyzed by using the GO enrichment tool. The results showed that the differential genes were located in the cell component associated with the synaptic connection of the cells (FIG. 5B), which was consistent with the position of the intercellular transmission of the viruses. The differential genes were significantly associated with the biological process of cell adhesion. The function participated in the establishment and maintenance of the cell connection (FIG. 5C, the differential threshold was set as log 2FoldChange<-1.5 and padj<0.05, or log 2FoldChange>1.5 and padj<0.05). According to the above results, the α-herpesvirus may promote the intercellular transmission of the viruses by deploying cytoskeletal proteins to induce the structure in which epithelial cells contacted with each other.

Example 7 Method for Establishing Cell Model for Specifically Studying Intercellular Transmission Mechanism of α-Herpesvirus by Using Human Liver Cancer Continuous Cell Line Huh7-C10

On the basis of differences between the human liver cancer continuous cell line Huh7-C10 and the commercial cell Huh-7 in the α-herpesvirus infection, information of host factors for regulating and controlling intercellular transmission of the α-herpesvirus was obtained by using genomics or proteomics.

What is claimed is:

1. An α-herpesvirus insensitive monoclonal cell strain, wherein the cell strain is a human liver cancer continuous cell line Huh7-C10 and deposited in the China General Microbiological Culture Collection Center with a deposit number of CGMCC NO. 45727 on Oct. 7, 2023.

2. The α-herpesvirus insensitive monoclonal cell strain according to claim 1, wherein the human liver cancer continuous cell line Huh7-C10 is insensitive when infected with an α-herpesvirus.

3. The α-herpesvirus insensitive monoclonal cell strain according to claim 2, wherein the insensitivity refers to an incapability of intercellular diffusion of the α-herpesvirus in the human liver cancer continuous cell line Huh7-C10.

4. The α-herpesvirus insensitive monoclonal cell strain according to claim 1, wherein the α-herpesvirus comprises herpes simplex virus type 1, bovine herpesvirus type 1 or porcine pseudorabies virus.

* * * * *